United States Patent
Froehlich et al.

(10) Patent No.: US 7,799,058 B2
(45) Date of Patent: Sep. 21, 2010

(54) INTERSPINOUS SPACER

(75) Inventors: Markus Froehlich, Balterswil (CH); Jochen Reinmuth, Winterthur (CH)

(73) Assignee: Zimmer GmbH, Winterthur (CH)

( * ) Notice: Subject to any disclaimer, the term of this patent is extended or adjusted under 35 U.S.C. 154(b) by 671 days.

(21) Appl. No.: 11/737,152

(22) Filed: Apr. 19, 2007

(65) Prior Publication Data

US 2008/0262617 A1 Oct. 23, 2008

(51) Int. Cl.
*A61B 17/70* (2006.01)
(52) U.S. Cl. .............. 606/248; 606/246; 623/17.11
(58) Field of Classification Search ......... 606/246–253, 606/60, 61, 90, 279; 623/14.12, 17.11–17.16
See application file for complete search history.

(56) References Cited

U.S. PATENT DOCUMENTS

| | | | |
|---|---|---|---|
| 5,496,318 | A | 3/1996 | Howland et al. |
| 5,645,599 | A | 7/1997 | Samani |
| 5,836,948 | A | 11/1998 | Zucherman et al. |
| 5,989,256 | A | 11/1999 | Kuslich et al. |
| 6,074,390 | A | 6/2000 | Zucherman et al. |
| 6,238,397 | B1 | 5/2001 | Zucherman et al. |
| 6,364,883 | B1 | 4/2002 | Santilli |
| 6,419,677 | B2 | 7/2002 | Zucherman et al. |
| 6,582,433 | B2 | 6/2003 | Yun |
| 6,733,534 | B2 | 5/2004 | Sherman |
| 6,946,000 | B2 | 9/2005 | Senegas et al. |
| 7,048,736 | B2 | 5/2006 | Robinson et al. |
| 7,087,083 | B2 | 8/2006 | Pasquet et al. |
| 7,101,375 | B2 | 9/2006 | Zucherman et al. |
| 2002/0095154 | A1 | 7/2002 | Atkinson et al. |
| 2005/0102028 | A1 | 5/2005 | Arnin et al. |
| 2005/0203512 | A1 | 9/2005 | Hawkins et al. |
| 2005/0261768 | A1 | 11/2005 | Trieu |
| 2006/0084988 | A1 | 4/2006 | Kim |
| 2006/0085070 | A1 | 4/2006 | Kim |
| 2006/0235386 | A1 | 10/2006 | Anderson |
| 2006/0241601 | A1 | 10/2006 | Trautwein et al. |
| 2006/0241610 | A1 | 10/2006 | Lim et al. |
| 2006/0241613 | A1 | 10/2006 | Bruneau et al. |
| 2006/0241614 | A1 | 10/2006 | Bruneau et al. |
| 2006/0271055 | A1 | 11/2006 | Thramann |
| 2006/0271194 | A1 | 11/2006 | Zucherman et al. |
| 2007/0005064 | A1 | 1/2007 | Anderson et al. |

(Continued)

FOREIGN PATENT DOCUMENTS

| | | |
|---|---|---|
| WO | 2006089085 A2 | 8/2006 |
| WO | 2006113080 A2 | 10/2006 |
| WO | 2006116853 A1 | 11/2006 |
| WO | 2007111979 A2 | 10/2007 |

*Primary Examiner*—Eduardo C Robert
*Assistant Examiner*—Christina Negrelli
(74) *Attorney, Agent, or Firm*—Crompton, Seager & Tufte, LLC.

(57) ABSTRACT

A spacer for maintaining separation between adjacent spinous processes having a first and second end support, a connecting member, and a central member positioned between the first and second end supports. The spacer is adjustable between a collapsed configuration and an expanded configuration such that when the connection member is pulled to bring the first and second end supports closer together, the central member expands into the expanded configuration to contact and support adjacent spinous processes.

24 Claims, 11 Drawing Sheets

U.S. PATENT DOCUMENTS

| | | |
|---|---|---|
| 2007/0016303 A1 | 1/2007 | Jackson |
| 2007/0250060 A1 | 10/2007 | Anderson et al. |
| 2007/0282340 A1 | 12/2007 | Malandain |
| 2008/0027438 A1 | 1/2008 | Abdou |
| 2008/0114367 A1* | 5/2008 | Meyer ........................ 606/90 |
| 2008/0177387 A1* | 7/2008 | Parimore et al. ......... 623/17.16 |

* cited by examiner

INTERSPINOUS SPACER

FIELD OF THE INVENTION

The present invention relates generally to devices for treating spinal stenosis, and more particularly to interspinous spacers that can be implanted in a minimally invasive manner to treat spinal stenosis.

BACKGROUND OF THE INVENTION

A large majority of the population will experience back pain at some point in their lives that results from a spinal condition. The pain may range from general discomfort to disabling pain that immobilizes the individual. One type of adverse spinal condition is spinal stenosis which occurs when the spinal canal or nerve root canals become too narrow and reduces the space for the passage of blood vessels and nerves.

Lumbar spinal stenosis ("LSS", and sometimes called sciatica) is a condition of the spine characterized by a narrowing of the lumbar spinal canal. With lumbar spinal stenosis, the spinal canal narrows and pinches the spinal cord and nerves, causing pain in the back and legs. It is estimated that approximately 5 in 10,000 people develop LSS each year. For patients who seek the aid of a physician specialist for back pain, approximately 12-15% are diagnosed as having LSS.

Several causes of spinal stenosis have been identified, including aging, heredity, arthritis, and changes in blood flow to the lower spine. Aging is believed to be the most common cause, because as a person ages the ligaments connecting the bones of the spine can thicken and spurs may develop on the bones and into the spinal canal. The cushioning discs between the vertebrae also frequently deteriorate, and the facet joints may begin to break down. Over time, loss of disk height in the lumbar regions can result in a degenerative cascade with deterioration of all components of a motion segment resulting in segment instability and ultimately in spinal stenosis. During the process of deterioration, disks can become herniated and/or become internally torn and chronically painful. When symptoms seem to emanate from both anterior (disk) and posterior (facets and foramen) structures, patients cannot tolerate positions of extension or flexion. Heredity is believed to play a role in some cases because it may cause some people to have a smaller than average spinal canal, typically leading to LSS symptoms even at a relatively young age.

The most common symptoms of spinal stenosis are pain and difficulty when walking, although numbness, tingling, hot or cold feelings in the legs, and weakness or tiredness may also be experienced. In extreme cases, spinal stenosis can cause cauda equina syndrome, a syndrome characterized by neuromuscular dysfunction that may result in permanent nerve damage.

Common treatments for LSS include physical therapy (including changes in posture), medication, and occasionally surgery. Changes in posture and physical therapy may be effective in flexing the spine to enlarge the space available to the spinal cord and nerves—thus relieving pressure on pinched nerves. Medications such as NSAIDS and other anti-inflammatory medications are often used to alleviate pain, although they are not typically effective at addressing the cause of the pain. Surgical treatments are more aggressive than medication or physical therapy, but in appropriate cases surgery may be the best way to achieve a lessening of the symptoms associated with LSS.

The most common surgery for treating LSS is decompressive laminectomy, in which the lamina of one or more vertebrae is removed to create more space for the nerves. The intervertebral disc may also be removed, and the vertebrae may be fused to strengthen unstable segments. The success rate of decompressive laminectomy has been reported to be in excess of 65%, with a significant reduction in LSS symptoms being achieved in many cases.

More recently, a second surgical technique has been developed in which the vertebrae are distracted and an interspinous spacer is implanted to maintain the desired separation between the segments. This technique is somewhat less invasive than decompressive laminectomy, but may provide significant benefits to patients experiencing LSS symptoms.

As with other surgeries, one consideration when performing surgery to implant an interspinous spacer is the size of the incision that is required to allow introduction of the device. Medical treatments that can be performed in a minimally invasive manner are greatly sought after by the medical community and patients alike. The term "minimally invasive" herein shall be understood as being accomplished by providing a technique less invasive than an open procedure to gain access to the application point. In some procedures, minimally invasive techniques are advantageous because there may be no need to resect tissue so that they can be performed with the use of a local anesthesia, have a shorter recovery period, result in little to no blood loss, and greatly decrease the chances of significant complications. Additionally, minimally invasive techniques are usually less expensive for the patient. Minimally invasive techniques are therefore generally preferred, but several interspinous spacers previously known in the art do not work well with minimally invasive surgical techniques. The implantation profile presented by known spacers precludes introduction through a very small incision. A need therefore exists for an interspinous spacer that can be implanted using minimally invasive surgical techniques.

SUMMARY OF THE INVENTION

This invention addresses these and other problems associated with the prior art by providing a spacing device and associated method to insert it into a medical patient in a minimally invasive procedure. In a first aspect of the invention, a spacer used for maintaining separation between adjacent spinous processes includes a first and second end support, a connecting member, and a central member positioned between the first and second end supports. The spacer is adjustable between a collapsed configuration and an expanded configuration such that when the connection member is pulled to bring the first and second end supports closer together, the central member expands into the expanded configuration. In the expanded configuration the spacer contacts and supports adjacent spinous processes.

In some embodiments of the invention, the central member is ellipsoidal. The central member may additionally include first and second halves having a cavity.

In another embodiment of the invention, the spacer further includes a center guide having a hole. The center guide may be positioned between the first and second end supports providing additional support to the center of the spacer when inserted between the spinal processes. In some embodiments, the connecting member may be a rod. The rod may be coupled to the first end support and extend through the hole in the center guide and the hole in the second end support. The rod is slidably translatable along the axis of the rod through the center guide and the second end support. Pulling the rod along its axis causes the central member to move from the collapsed configuration to the expanded configuration.

In some embodiments, the rod further includes a first plurality of engaging teeth and a predetermined breaking point located near the engaging teeth and the second end support further includes a first plurality of engaging teeth in the hole. The engaging teeth of the rod are configured to contact the engaging teeth of the second rigid end support thereby preventing the rod from translating toward the collapsed configuration and maintaining the central member in the expanded configuration. In other embodiments, the second end support further includes a second plurality of engaging teeth positioned in the hole opposing the first plurality of engaging teeth and the rod further includes a second plurality of engaging teeth configured to align with the engaging teeth of the second end support. The engaging teeth are configured such that when the engaging teeth of the second end support and the rod come out of contact, the central member returns to the collapsed configuration.

In a second aspect of the invention, a spacer used for maintaining separation between adjacent spinous processes includes a first and second end support, a center support, a connecting member, and at lease one central member positioned between the first and second end supports. The center support is positioned between the adjacent spinous processes. The spacer is adjustable between a collapsed configuration and an expanded configuration such that when the connection member is pulled to bring the first and second end supports closer together toward the center support, the central member expands into the expanded configuration to contact and support adjacent spinous processes.

In another embodiment of the invention, the center support encloses a portion of the central member such that the central member forms a first and second flangular portion on opposing sides of the center support in the expanded configuration. The central member is a fabric material and the spacer is held in place by contacting at least one side of the spinous processes with the first and second flangular portions of the expanded configuration.

In an alternate embodiment of the invention, the spacer further includes first and second center members. A plurality of spoke members extend from the center support and connect to a flangular member comprising the first or second center member. The center of the flangular member is connected to one of the first and second end supports such that the flangular member expands from a collapsed configuration to an expanded configuration when the first and second end supports are moved toward the center support. The spacer is held in place by contacting at least one side of the spinous processes with the first and second center members in the expanded configuration.

In another aspect of the invention, a spacer configured as an annular repair device includes a first rigid end support, an ellipsoidal first section containing a cavity, deformable between a first undeformed position and a second deformed position, a flangular second section coupled to the ellipsoidal first section opposite the first rigid end support, a second rigid end support with a hole surrounded by the second section and projecting into the cavity of the first section, and a rigid rod. The rod is coupled to the first rigid end support and extends through the hole in the second end support. The rod is slidably translatable along the axis of the rod through the second end support. Translating the rod along its axis causes the first ellipsoidal section to move from the first undeformed position to the second deformed position.

As a result of the various embodiments and aspects of this invention, an interspinous spacer can be surgically implanted in a collapsed configuration through a minimally invasive procedure and then expanded between an adjacent pair of the patient's spinous processes.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

An interspinous spacer is designed to maintain a minimal distance between the spinous processes of adjacent vertebrae. As such, the spacer typically has a blocking portion that keeps the vertebrae from coming together. In general, the blocking portion maintains a distance of approximately one-quarter inch to one-half inch between the spinous processes. Additionally, the spacer may be designed to fit snugly around the spinous processes to avoid being dislodged by movement of the spine.

Figure 1:
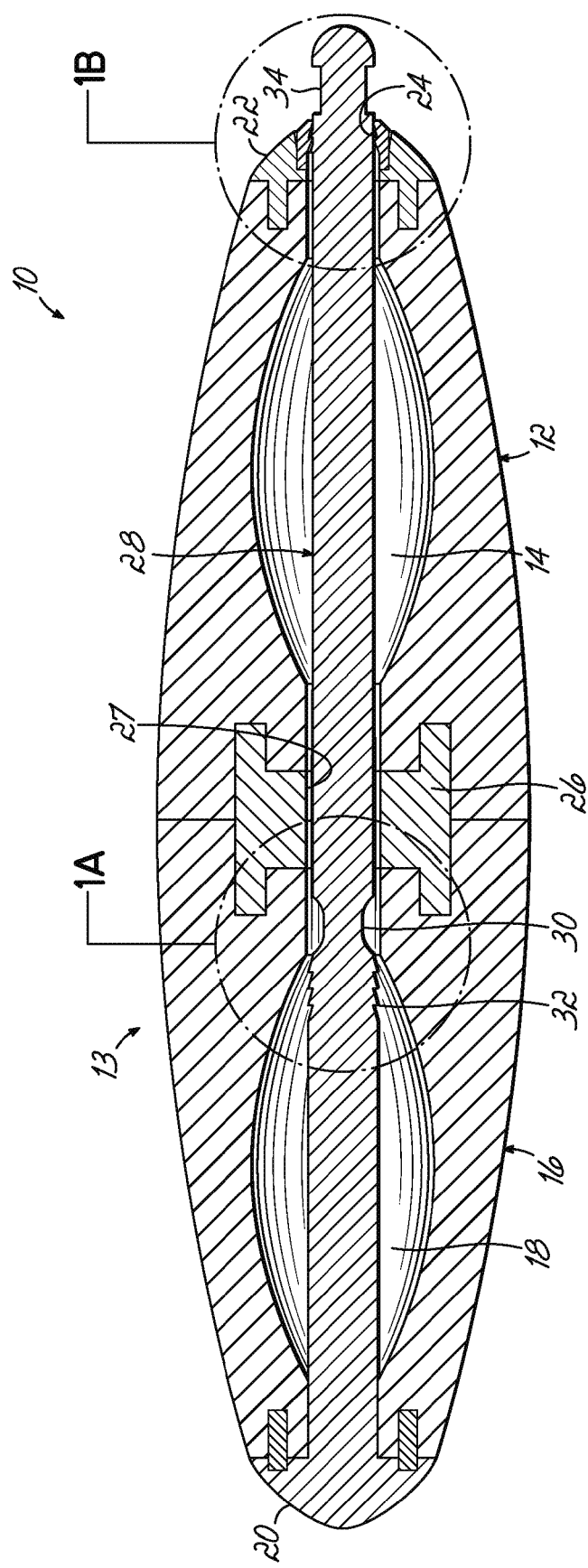
FIG. 1 shows a cross sectional view of one embodiment of a spacer consistent with the present invention.
Figure 1B:
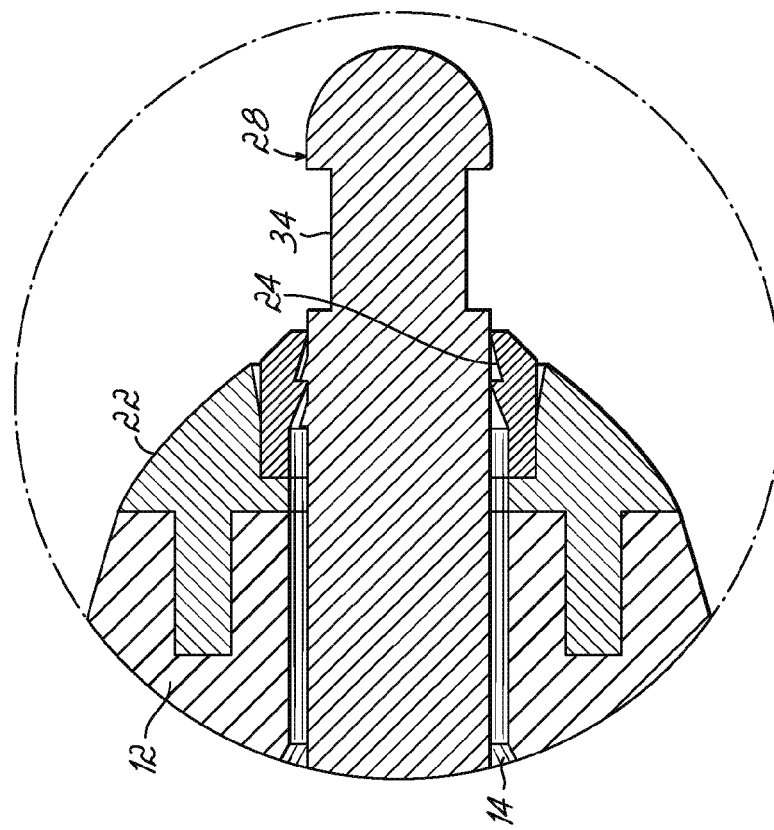
FIG. 1B shows additional detail of a different portion of the spacer of FIG. 1.
Figure 1A:
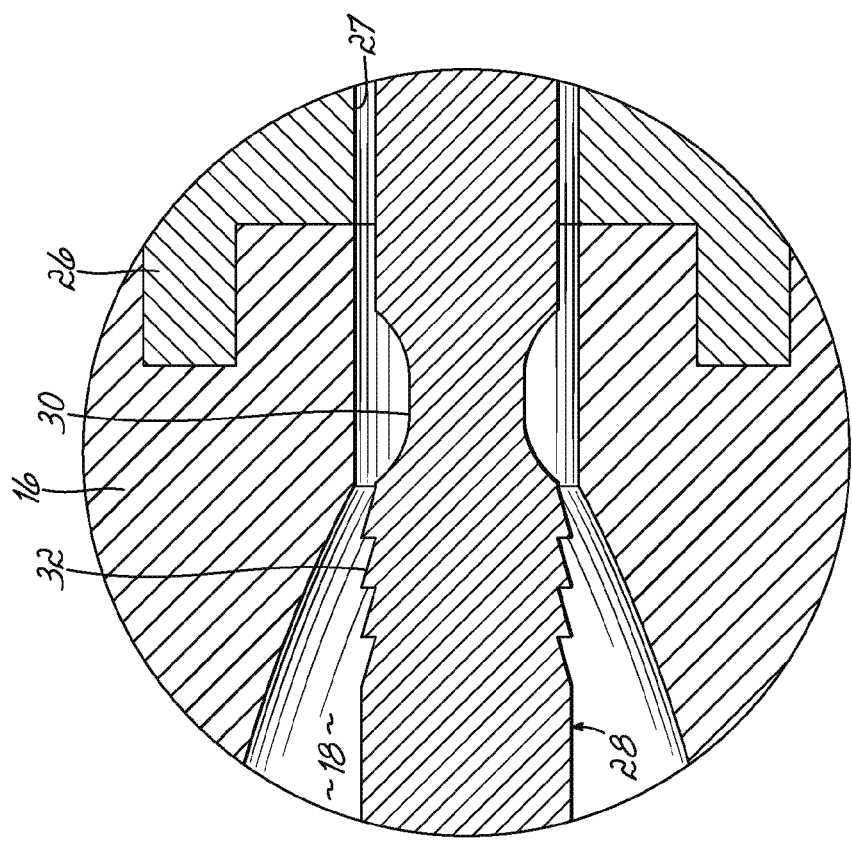
FIG. 1A shows additional detail of a portion of the spacer of FIG. 1.

Turning now to the drawings, wherein like numbers denote like parts throughout the several views. FIG. 1 illustrates an exemplary spacer consistent with the invention. The spacer 10 has a first end support 20 and a second end support 22 on opposite ends of a central member 13 which may be composed of two half ellipsoidal sections 12, 16. Alternatively, the central member 13 may be formed of a single unit. Each half section has a cavity 14, 18. The two half sections 12, 16 may be joined at the center forming an ellipsoid. The ellipsoidal shape of the central member in the collapsed configuration allows for a minimally invasive insertion into a medical patient. Once inserted, the central member is configured so that each half section 12, 16 expands radially when the end supports 20, 22 are brought closer together. The radial expansion of the half sections 12, 16 forms a flangular shape, allowing the spacer to contact adjacent spinous processes, holding the spacer in place. The cavities 14, 18 in each half section 12, 16 may be offset such that one wall of the half section 12, 16 is thinner than the other wall to allow one side to collapse before the other. This configuration may facilitate the move from the collapsed ellipsoidal configuration to the expanded flangular configuration.

A connecting member 28 is coupled to the first end support 20 extending through the central member and through a hole 24 in the second end support with a portion of the connection member 28 extending therefrom. A center guide 26 is disposed between the central members 12 and 16 with a hole 27 through which the connecting member 28 extends. The center guide 26 provides additional support in the center of the spacer 10 in its expanded configuration.

Figure 2B:
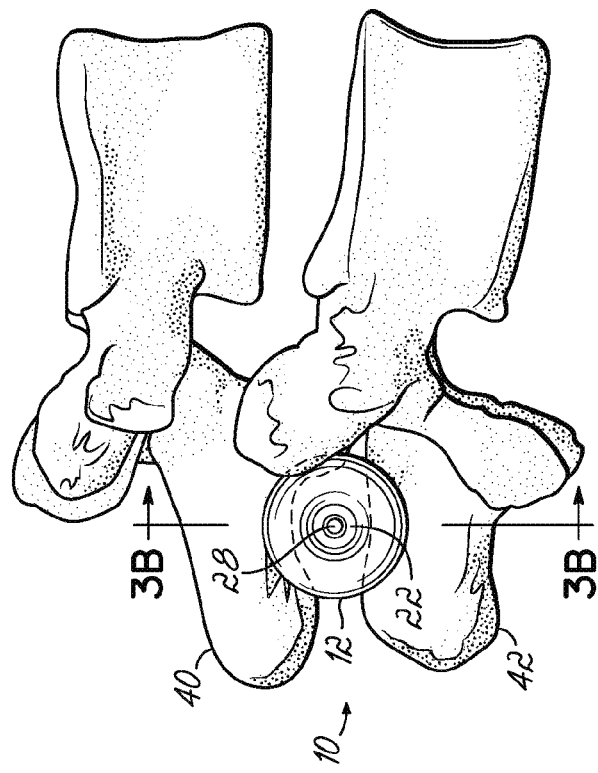
FIG. 2B shows the spacer of FIG. 2A in its expanded configuration between two adjacent spinal processes.
Figure 2A:
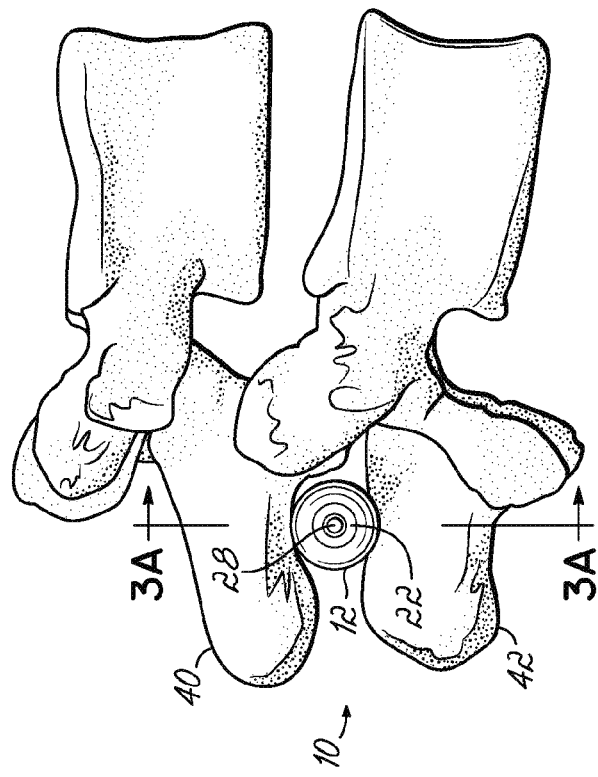
FIG. 2A shows an end view of the spacer of FIG. 1 in its collapsed configuration between two adjacent spinal processes.

The spacer 10 may be inserted between adjacent spinous processes 40, 42 as shown in FIGS. 2A and 2B. The spacer 10, may be inserted in its collapsed configuration as is consistent with the method of insertion of the invention. Once the spacer 10 has been inserted, the connecting member 28 of the spacer 10 is coupled with a cannula 50 (FIG. 3A) and pulled bringing the first end 20 closer to the second end 22, thereby moving the spacer 10 from its collapsed configuration to its expanded configuration. In the expanded configuration, the central member sections 12 and 16 may become flangular in shape and contact adjacent sides of the spinal processes 40, 42 holding the spacer 10 in place.

Figure 3A:
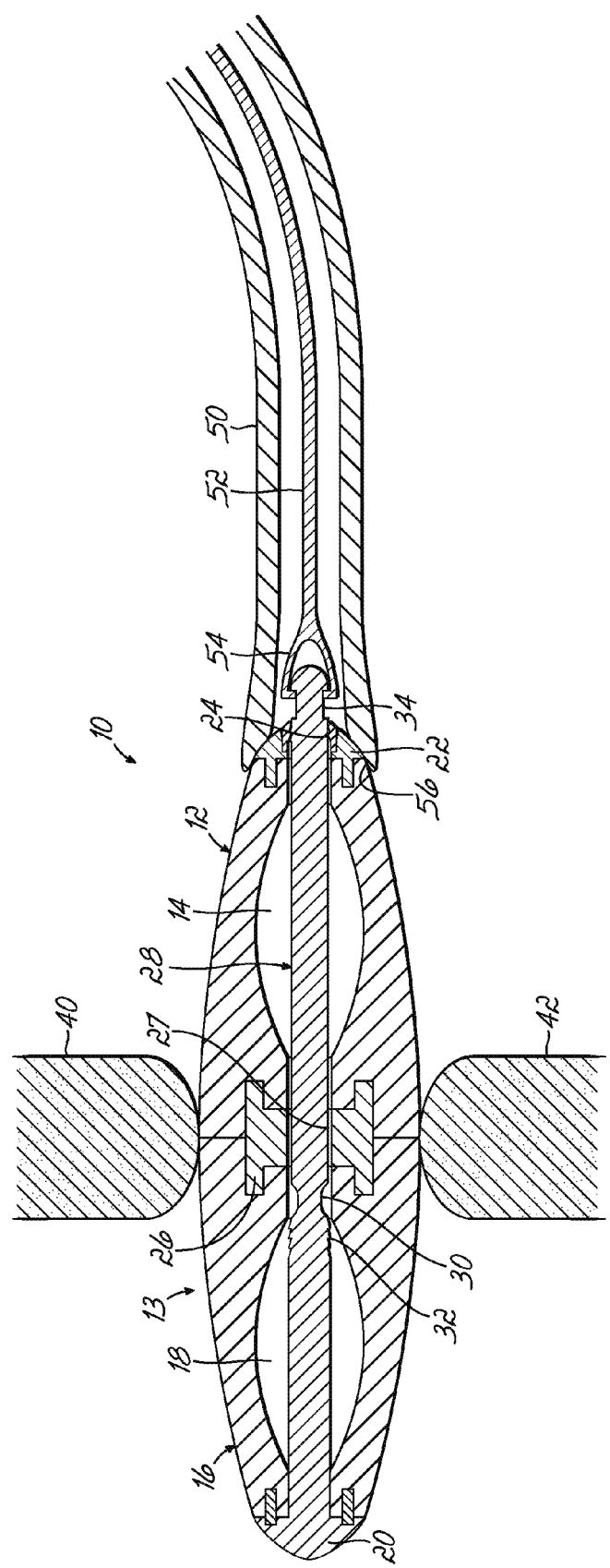
FIG. 3A shows a cross sectional view of the spacer of FIG. 1 in its collapsed configuration coupled with a connecting member and associated cannula.
Figure 3B:
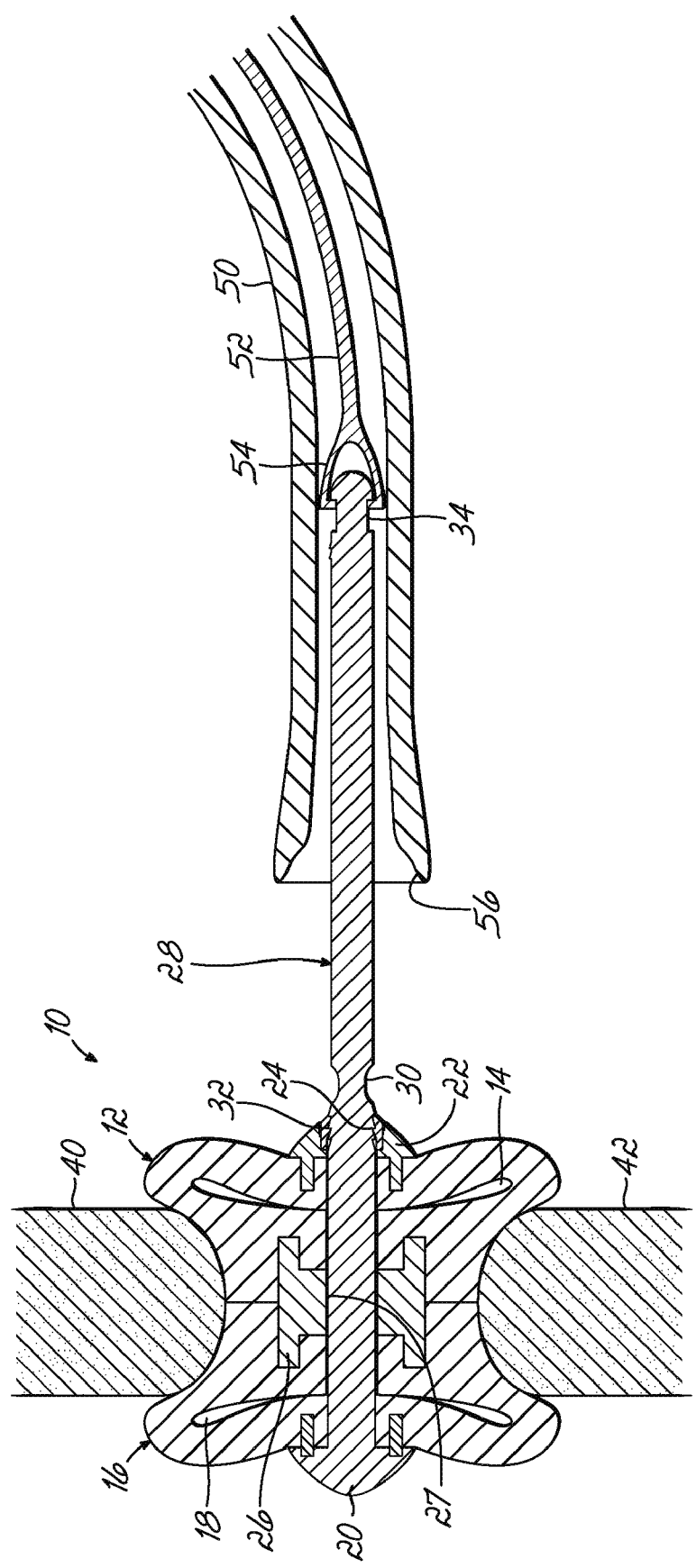
FIG. 3B shows a cross sectional view of the spacer of FIG. 3A in its expanded configuration coupled with the connecting member.

Referring now to FIG. 3A, the cannula 50 contains an inner cable 52 that is capable of coupling to the end of a portion of the connecting member 28 that extends from the second end support 22. The extended portion may have a recessed area 34 by which the end 54 of the inner cable 52 may attach and hold the end of the connecting member 28. The cannula 50 holds the spacer 10 at the second end 22 with edges 56 configured to mate with the second end 22. As the cable 52 of the cannula 50 is retracted, it pulls the connecting member 28 forcing the first end 20 closer to the second end 22. As the ends are pulled closer together, the half ellipsoidal central members 12, 16 deform expanding radially into a flangular configuration and contact adjacent edges with the spinous processes 40, 42 as can be seen in FIG. 3B.

Figure 3C:
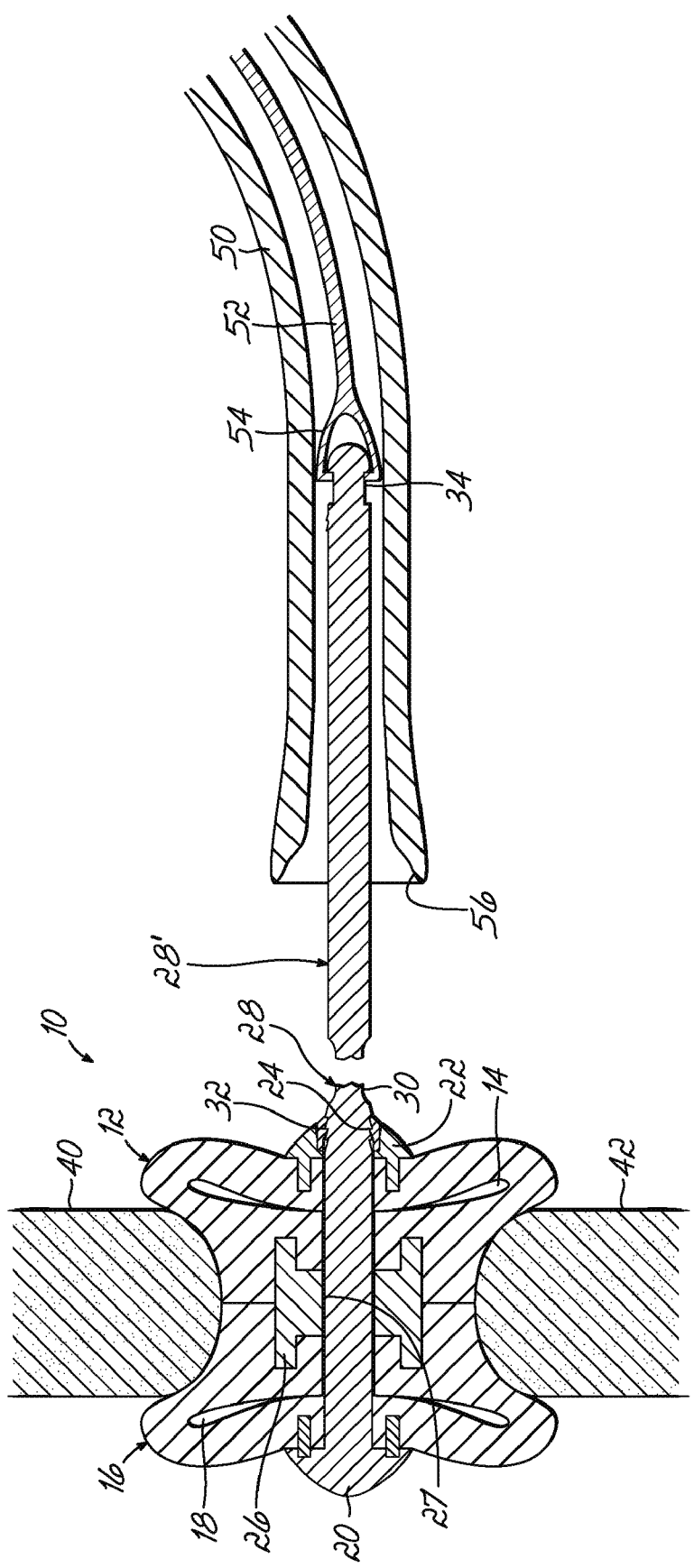
FIG. 3C shows a cross sectional view of the spacer of FIG. 3B after breaking away a portion of the connecting member.

The connecting member 28 may contain a predetermined breaking point 30, which allows for an excess portion 28' of the connecting member 28 to be discarded after the spacer 10 is moved to its expanded configuration. The connecting member 28 may also contain a locking mechanism or device that holds or maintains the spacer 10 in its expanded configuration. In one embodiment, the locking mechanism may include a plurality of engaging teeth 32 which are configured to contact engaging teeth 24 of the second end support. When the teeth 24, 32 are engaged, the spacer 10 maintains its expanded configuration. After the engaging teeth 24 of the connecting member 28 contact the engaging teeth 32 of the second end 22, the excess portion 28' of the connecting member 28 may be broken off as shown in FIG. 3C. The teeth 32 may be located along any portion of the connecting member. For example, the teeth 32 may be located more proximal to end support 22 that results in an implant with a different shape profile and, in some embodiments, a different amount of distraction to the spinous processes. It is possible to provide a surgeon with a kit that includes a number of spacers 10 of different sizes as well as teeth 32 locations, allowing the surgeon to choose the appropriate spacer 10 for the patient. In an alternate embodiment, the engaging teeth 32 of the connecting member 28 and the engaging teeth 24 of the second end support are partially disposed along opposite sides of the connecting member 28 and the second end support 22. This partial distribution allows for a releasable engagement of the teeth 24, 32 such that twisting or turning the connecting member 28 disengages the teeth 24, 32. Once the teeth 24, 32 are disengaged, the spacer 10 is allowed to return to the collapsed configuration. In other embodiments, other devices, other than engaging teeth, may be used to maintain the spacer 10 in the expanded configuration. For example, a pin-hole configuration or adhesive may be used. In another embodiment, the connecting member 28 may include threads instead of engaging teeth that mate with threads on the end support 22 to adjustably hold or maintain the spacer in the expanded configuration. In this embodiment, the connecting member 28 may be rotated as desired to adjust the relative positions of the end supports 20, 22 and, thus, allow for simple alteration of the final configurations or shape profile of the spacer 10 to achieve a desired distraction between the spinous processes. This threaded design may also allow for revision of the implant shape profile or easy removal of the implant at a later date.

Optionally, the connecting member 28 may include an expanded portion, an area of greater cross-sectional diameter or width, along its length. This expanded portion may be located within either cavity 14, 18 and provides a positive stop upon movement of the spacer 10 into the expanded configuration. This stop would prohibit the plurality of teeth 32 of the connecting member 28 from passing beyond the engaging teeth 24 of the second end support 22 and the over-compression of the spacer.

The spacer 10 may be made of materials such as PCU (80A or 55B) and PEEK. PCU is elastic material allowing for damping. PCU may be suitable for the half ellipsoidal central member sections 12, 16. The end support 20, 22, connecting member 28, and center guide 26 may require more rigidity than the half pieces of the central member. These members may therefore be composed of the PEEK material. Other suitable flexible materials may be used in the construction of the spacer 10. The spacer 10 may also be made of a flexible metal material, such as nitinol, that may be predisposed to the shape of the spacer 10 in its expanded configuration and held in the collapsed configuration during implantation. The spacer is released from its collapsed configuration after positioning between the spinous processes. In this embodiment, teeth 32 may be aligned with teeth 24 of the second end support 22 when the spacer 10 is in its collapsed configuration. As the connecting member 28 is pulled bringing the first end 20 closer to the second end 22, the teeth 24, 32 disengage from one another allowing the spacer 10 to move to its pre-disposed expanded configuration.

The spacer 10 having the shape of an ellipsoid before it is placed in the medical patient coupled with the flexibility of the PCU material composing the central member allow for a minimally invasive surgical procedure performed under local anesthesia. The ability of the spacer 10 to change its shape after insertion into the expanded configuration consisting of two flangular-type arrangements on both sides of the spinous processes holding the device in place allows for smaller incisions consistent with minimally invasive procedures.

Figure 4A:
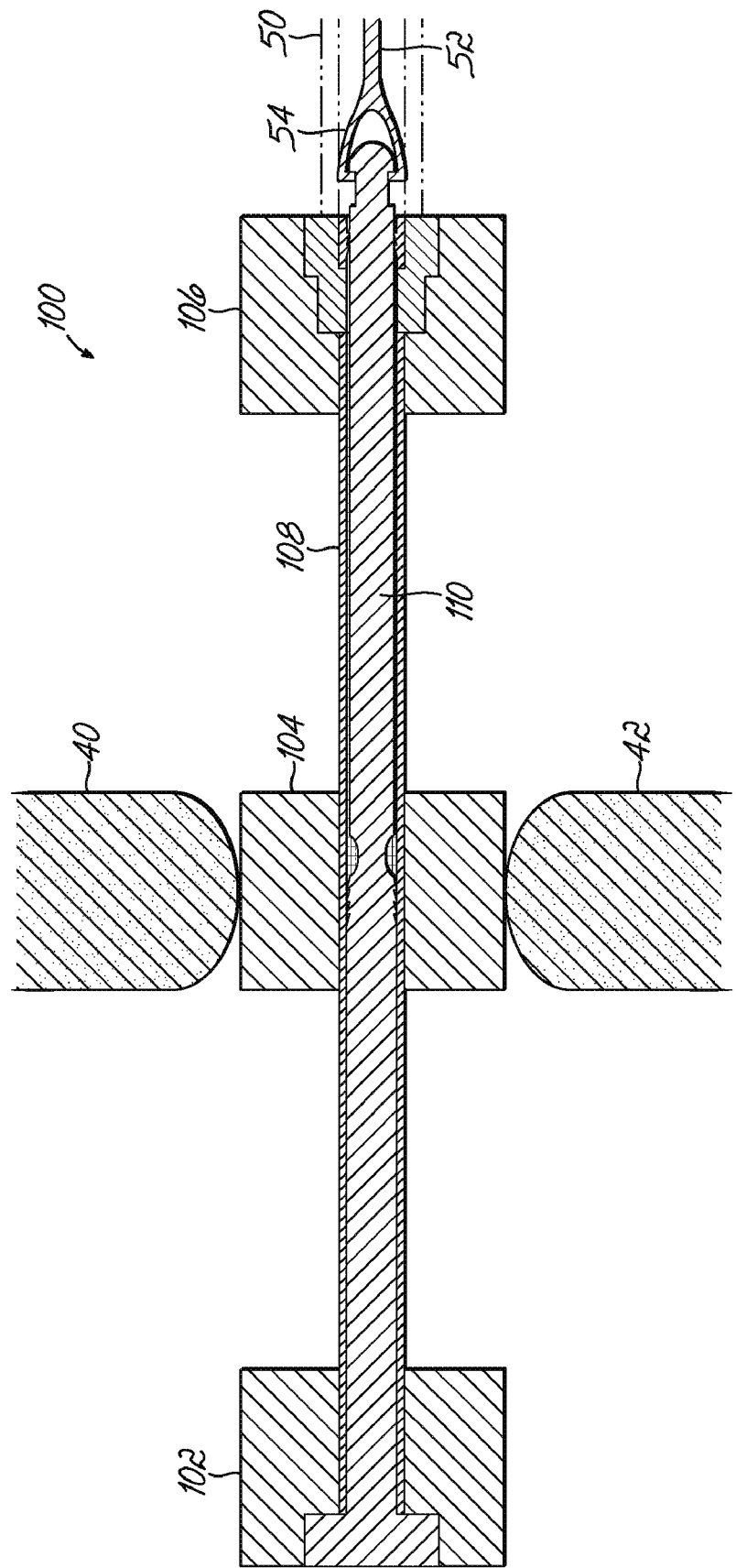
FIG. 4A shows an alternate embodiment of the spacer consistent with the invention in its collapsed configuration.
Figure 4B:
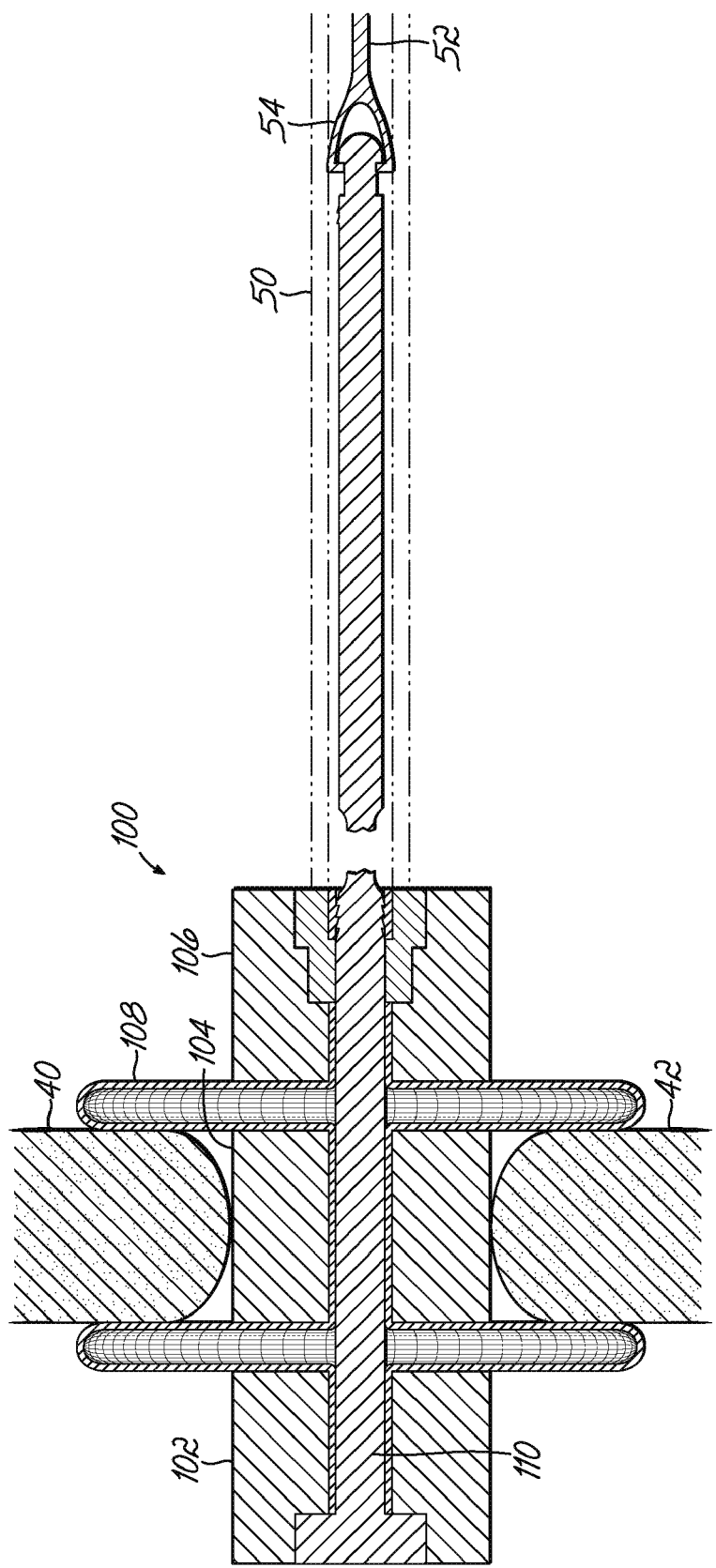
FIG. 4B shows the spacer of FIG. 4A in situ in its expanded configuration.

In an alternate embodiment of the spacer 100 as shown in FIGS. 4A and 4B, three supports 102, 104, 106 each having a hole are spaced at distances apart from one another. A connecting member 110 is surrounded by an expandable material 108, for example a mesh fabric or mesh flexible material like nitinol, and inserted through each of the spacing supports 102, 104, 16. As the connecting member 110 is pulled, supports 102 and 106 are moved towards the center support 104 causing the mesh material 108 to expand. The expansion forms flange-like sections that contact adjacent sides of the spinous processes 40, 42 holding the spacer 100 in place. In the case of an expandable member made of nitinol, the expandable member may have a preferred expanded configuration such that upon pulling the connecting member 110, the expandable member 108 will naturally move to the preferred expanded configuration. A clamping mechanism (not shown) may be utilized to hold the end supports 102 and 106 in place, maintaining the expanded position of the expandable material. In one embodiment, the expandable material may be filled with a material, such as a polymeric flowable material, that hardens within the expandable material. While a clamping member may be utilized for this particular embodiment, any means of preventing the two support members 102 and 106 from returning to the collapsed position of the spacer may be used.

Figure 5A:
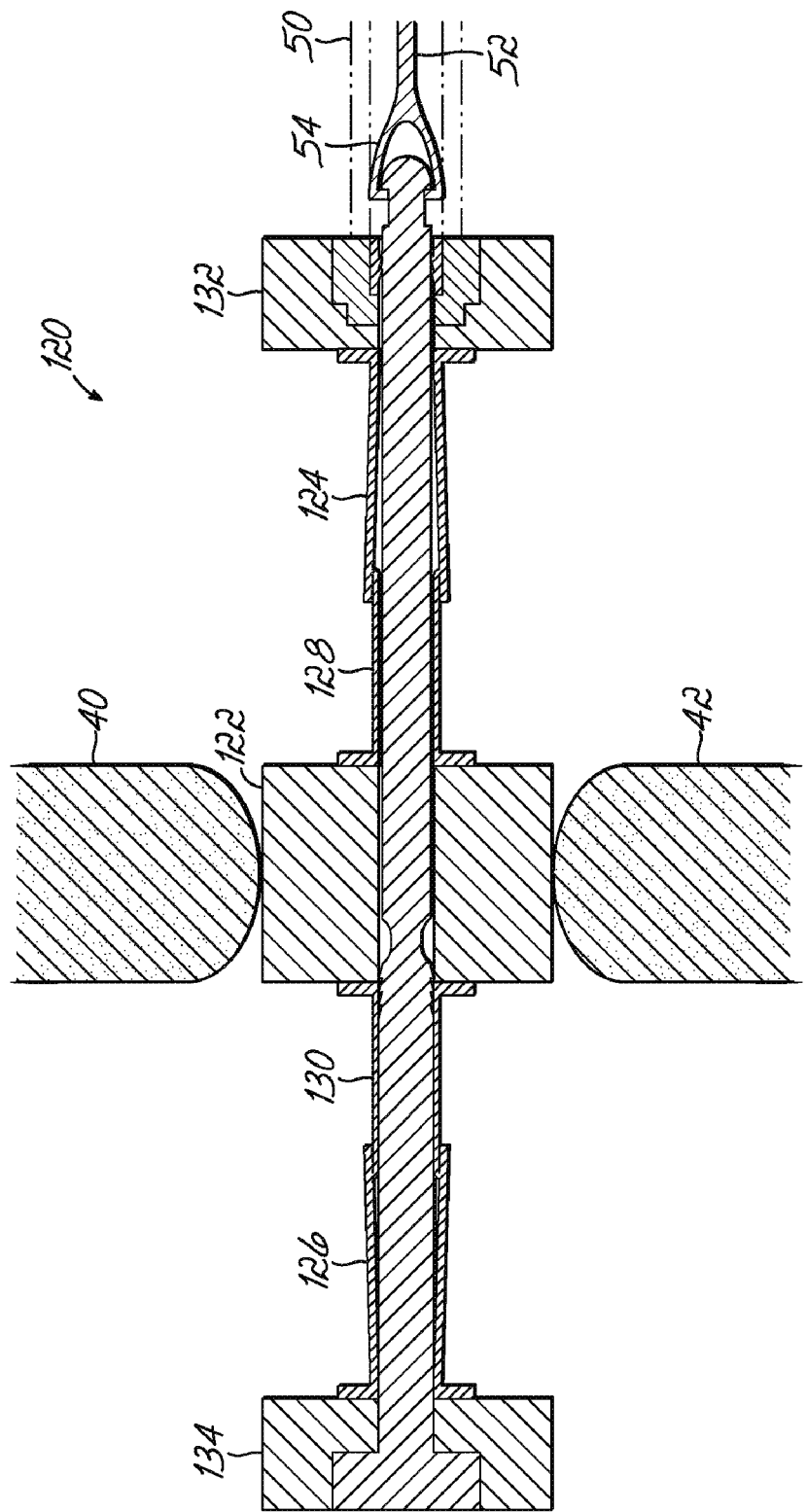
FIG. 5A shows an alternate embodiment of the spacer consistent with the invention in its collapsed configuration.
Figure 5B:
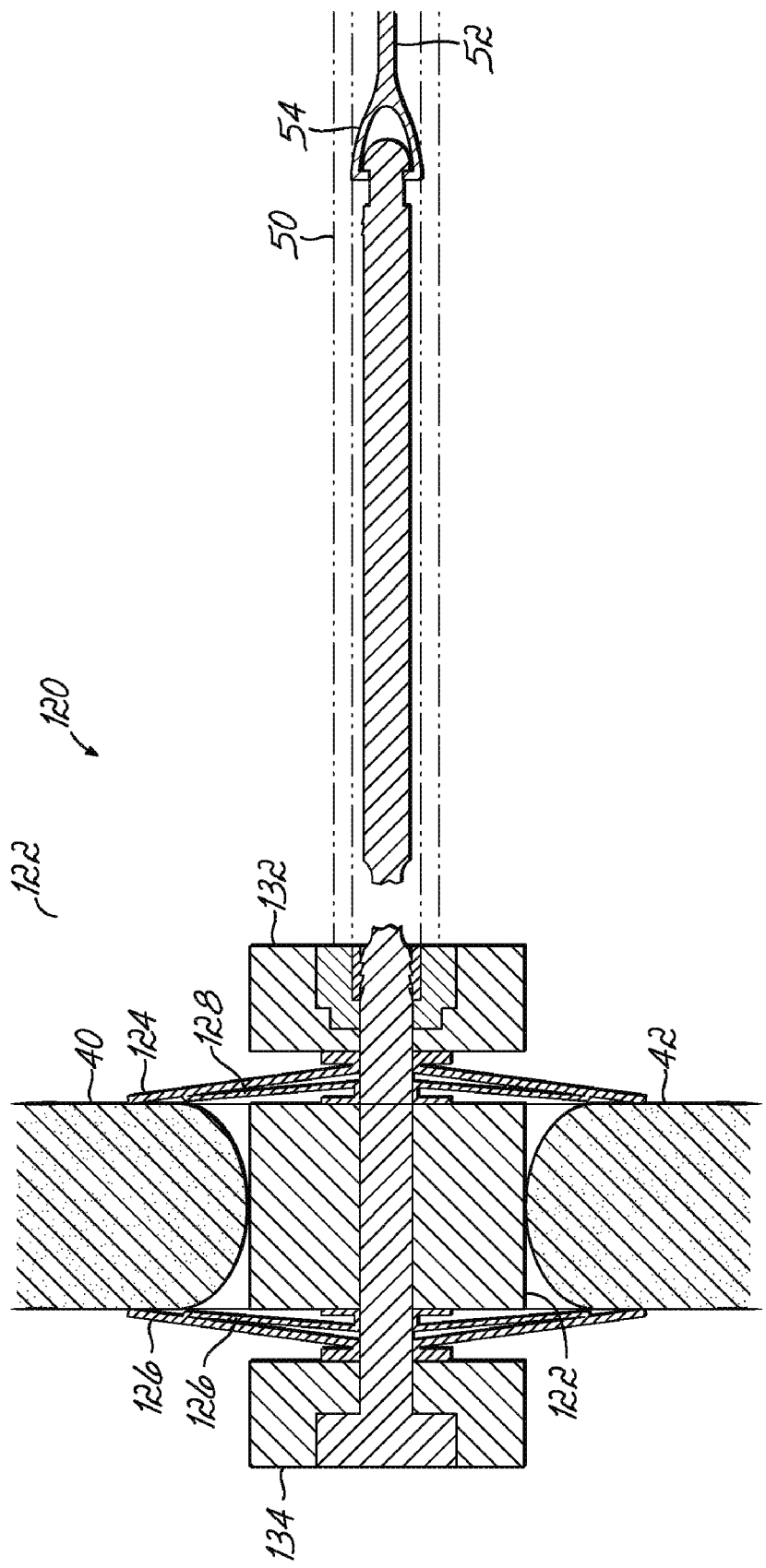
FIG. 5B shows the spacer of FIG. 5A in situ in its expanded configuration.

In another embodiment of the present invention as shown in FIGS. 5A and 5B, a spacer 120, is comprised again of a center support member 122 with flangular-type members 124 and 126 which are expandable from a collapsed configuration to an expanded configuration. An end support 132 on the end of flangular member 124 connects to a central connecting member which extends through the spacer 120 and out through a second end support 134. As the connecting member is pulled, forcing the end supports 132 and 134 to come closer together, a plurality of spoke type members 128 and 130 cause the flangular members 124 and 126 to expand on either side of the spinous processes 40, 42. The center support member is situated between the spinous processes and in the expanded form members 124 and 126 hold the spacer in place. A snap-type configuration in the second end support 134 may hold the spacer 120 in place preventing the members 124 and 126 from returning to their collapsed positions.

Figure 6B:
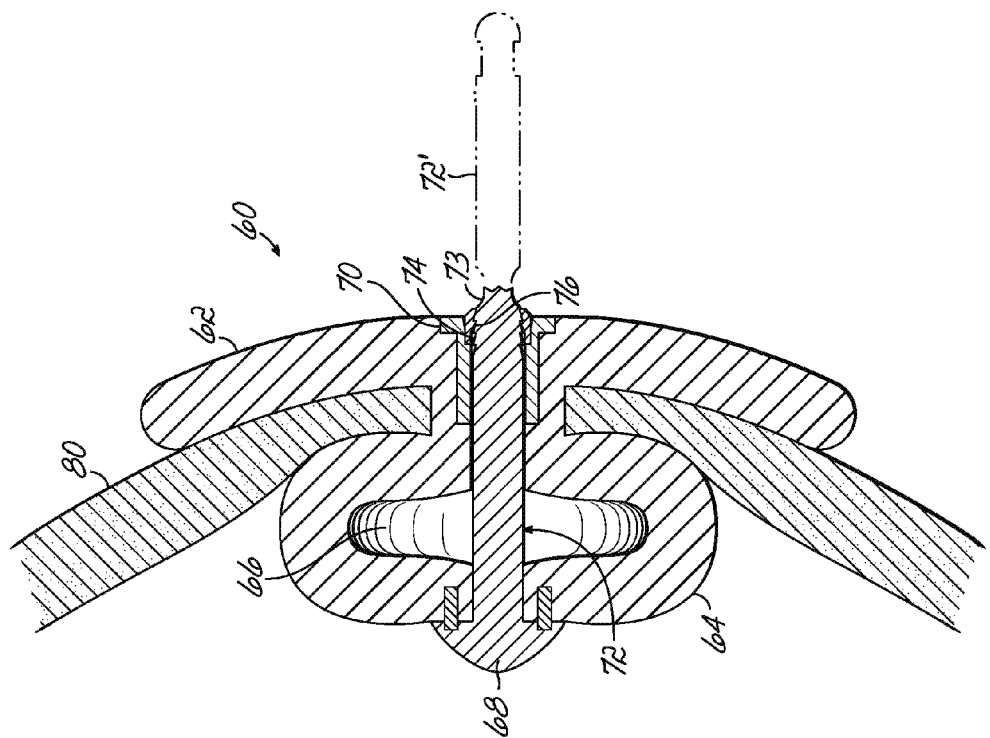
FIG. 6B shows a cross section of the spacer of FIG. 4A in its expanded configuration.
Figure 6A:
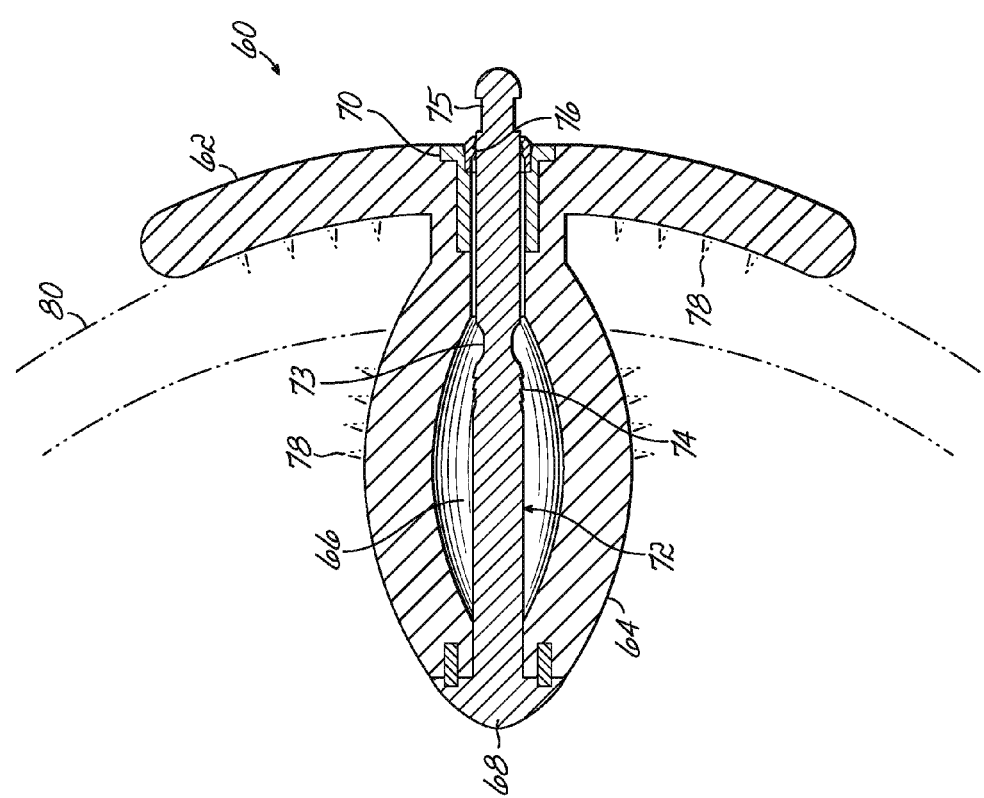
FIG. 6A shows a cross section of an alternate embodiment of the spacer in its collapsed configuration for annular repair consistent with the invention.

In still another embodiment of the present invention, the spacer may be configured for an annular repair. As seen in FIGS. 6A and 6B, the spacer 60 has a first rigid end support 68 which is coupled to an ellipsoidal first section 64 containing a cavity 66. A flangular second section 62 is coupled to the ellipsoidal first section 64 opposite from the first rigid end support 68. A second rigid end support 70 is disposed within the flangular second section containing a hole through which a connecting member 72 extends. The connecting member 72 is coupled to the first end support 68 and is configured to deform the ellipsoidal member 64 when it is pulled. The ellipsoidal member deforms radially from the ellipsoidal collapsed configuration to a flangular type expanded configuration.

The connecting member 72 contains a predetermined breaking point 73 to allow the excess portion 72' of the connecting member 72 to be broken off and disposed of after the ellipsoidal member is in the expanded configuration. The connecting member 72 also contains a plurality of engaging teeth 74, which are configured to match a set of engaging teeth 76 disposed in the second end support 70. When the connecting rod 72 is pulled, expanding the ellipsoidal section 64 into the expanded configuration, the engaging teeth 74 and 76 hold the spacer in place. At that point, the excess portion 72' of the connecting member 72 may be broken off as seen best in FIG. 4B. In other embodiments, other devices, other than engaging teeth, may be used to maintain the spacer 60 in the expanded configuration. For example, a pin-hole configuration or adhesive may be used.

The spacer 60 may be inserted through a hole in its collapsed configuration. The flangular second portion 62 contacts the tissue 80 preventing the spacer from being pushed through the hole. As the spacer 60 is expanded, the expanded configuration of the first ellipsoidal portion becomes flangular in shape and contacts the tissue 80 sealing the hole and providing support to the surrounding area, thereby preventing the spacer from being removed. Optional projections 78 may be disposed along the outside of the ellipsoidal first member and the flangular second member to assist in engaging the surrounding tissue and holding the spacer in place. In other embodiments the projections may be replaced with spikes or ribs.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of applicants' general inventive concept.

What is claimed is:

1. A spacer for maintaining separation between adjacent spinous processes, the spacer comprising:
    first and second end supports, the second end support having a hole therethrough and a first plurality of engaging teeth at least partially disposed along the hole;
    a connecting member having a first plurality of engaging teeth and;
    at least one expandable member at least partially surrounding a portion of the connecting member; and
    a central member with a hole therethrough positioned between the first and second end supports;
    wherein the connecting member is coupled to the first end support and extends through the hole in the central member and the hole in the second end support, the connecting member being slideably translatable through the central member and the second end support, wherein pulling the connecting member along its axis causes the connecting member to move the spacer between a collapsed configuration and an expanded configuration by bringing the first and second end supports closer together, wherein the engaging teeth of the connecting member are configured to contact the engaging teeth of the second end support thereby preventing the connecting member from translating toward the collapsed configuration and maintaining the spacer in the expanded configuration, wherein at least a portion of the expandable member expands into the expanded configuration to contact and support adjacent spinous processes.

2. The spacer of claim 1 wherein the connecting member further comprises a predetermined breaking point located near the engaging teeth, the breaking point structured to allow an excess portion of the connecting member to be broken off after the engaging teeth of the connecting member contact the engaging teeth of the second end support and the spacer is in the expanded configuration.

3. The spacer of claim 2 wherein the second end support further comprises a second plurality of engaging teeth partially disposed along the hole and opposing the first plurality of engaging teeth and wherein the connecting member further comprises a second plurality of engaging teeth disposed on an opposite side of the connecting member from the first plurality of engaging teeth, configured to align with the engaging teeth of the second end support such that when the connecting member is turned, the first and second plurality of engaging teeth of the second end support and the connecting member come out of contact allowing the spacer to return to the collapsed configuration.

4. The spacer of claim 1 wherein the first and second end supports, and the central member are rigid.

5. The spacer of claim 4 wherein the first and second end supports, and the central member are composed of PEEK material.

6. The spacer of claim 1 wherein the central member is composed of PCU material.

7. The spacer of claim 1 wherein the central member is ellipsoidal.

8. The spacer of claim 1 wherein the expandable member comprises a mesh material.

9. The spacer of claim 8 further comprising:
a flowable material within the expandable member.

10. The spacer of claim 9 wherein the flowable material is capable of hardening to form at least one flangular member such that the flangular member expands from a collapsed configuration to an expanded configuration when the first and second end supports are moved toward the connecting member.

11. The spacer of claim 1 wherein the expandable member comprises first, second, third, and fourth expandable members, wherein the first and second expandable members are positioned between the first end support and the central member and the third and fourth expandable members are positioned between the central member and the second end support, wherein pulling on the connecting member causes the first and second expandable members to move toward each other and the third and fourth expandable members to move toward each other, wherein when the spacer is in the expanded configuration, at least the first and fourth expandable members contact the spinous processes.

12. The spacer of claim 11 wherein the first, second, third, and fourth expandable members form flanges in the expanded configuration.

13. The spacer of claim 11 wherein the first and fourth expandable members are disposed adjacent the first and second end supports, respectively, and the second and third expandable members are disposed adjacent opposite sides of the center support.

14. The spacer of claim 11 wherein when the spacer is in the collapsed configuration, at least a portion of the second and third expandable members extend between the first and fourth expandable members and the connecting member, respectively.

15. The spacer of claim 11 wherein when the spacer is in the collapsed configuration, an end portion of the first expandable member overlaps an end portion of the second expandable member, and an end portion of the fourth expandable member overlaps an end portion of the third expandable member.

16. The spacer of claim 11 wherein when the connecting member is pulled, the second and third expandable members cause the first and fourth expandable members to expand, respectively.

17. A method of implanting an interspinous spacer between adjacent spinous processes, the method comprising:
introducing a spacer that is configurable between an undeformed configuration and an expanded deformed configuration into a medical patient while the spacer is in the undeformed configuration, wherein the undeformed confivration is ellipsoidal presenting a minimal implantation profile to facilitate a minimal invasive surgical procedure;
pulling a member of the spacer causing the spacer to assume the expanded deformed configuration while in the medical patient, wherein the expanded configuration spacer is positioned between adjacent spinous processes; and
contacting at least one side of each of the spinous processes with the spacer in the expanded configuration to hold the spacer in place.

18. The method of claim 17 wherein the expanded deformed configuration comprises a first and second flangular portion and wherein holding the spacer in place comprises contacting at least one side of the spinous processes with the first and second flangular portions of the expanded deformed configuration.

19. A spacer for maintaining separation between adjacent spinous processes, the spacer comprising:
a first end support;
a first section containing a cavity, the first section deformable between a first undeformed position and a second deformed position, wherein the first end support is coupled to and forms an end of the first section;
a second section containing a cavity, the second section deformable between a first undeformed position and a second deformed position, wherein the first and second sections are each half of an ellipsoid and are juxtaposed to form an ellipsoid;
a second end support containing a hole, wherein the second end support is coupled to and forms an end of the second section; and
a connecting member, coupled to the first end support and extended through the hole in the second end support, wherein the connecting member is slideably translatable along the axis of the connecting member through the second end support, and wherein translating the connecting member along its axis causes the first and second sections to move from the first undeformed position to the second deformed position.

20. The spacer of claim 19 further comprising a reinforcing center guide with a hole positioned between and surrounded by the first and second sections, wherein the connecting member extends through the hole in the center guide, and wherein the connecting member is slideably translatable along the axis of the connecting member through the center guide.

21. The spacer of claim 20 wherein the center guide is rigid.

22. The spacer of claim 19 wherein the first and second end supports are rigid.

23. The spacer of claim 22 wherein the connecting member further comprises a plurality of engaging teeth and a predetermined breaking point located near the engaging teeth, and wherein the second rigid end support contains a plurality of engaging teeth in the hole, and further wherein the engaging teeth of the connecting member are configured to contact the engaging teeth of the second rigid end support thereby preventing the connecting member from translating back and maintaining the first and second end sections in their second deformed position.

24. The spacer of claim 23 wherein a portion of the connecting member is configured to be broken off after the engaging teeth of the rod contact the engaging teeth of the second rigid end support.

* * * * *

UNITED STATES PATENT AND TRADEMARK OFFICE
CERTIFICATE OF CORRECTION

PATENT NO. : 7,799,058 B2 Page 1 of 1
APPLICATION NO. : 11/737152
DATED : September 21, 2010
INVENTOR(S) : Markus Froehlich et al.

It is certified that error appears in the above-identified patent and that said Letters Patent is hereby corrected as shown below:

Column 10
Line 1 delete "confivration", and insert therefor -- configuration --.

Signed and Sealed this

Ninth Day of November, 2010

David J. Kappos
*Director of the United States Patent and Trademark Office*